(12) United States Patent
Abidin et al.

(10) Patent No.: US 9,414,828 B2
(45) Date of Patent: Aug. 16, 2016

(54) INTEGRATED RETRACTOR-DISTRACTOR SYSTEM FOR USE WITH MODULAR BONE SCREWS

(71) Applicant: BLACKSTONE MEDICAL, INC., Lewisville, TX (US)

(72) Inventors: Cin K. Abidin, Plano, TX (US); Brad Elmer, Lantana, TX (US); Sheeraz Qureshi, New York, NY (US); Nomaan Ashraf, New York, NY (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 174 days.

(21) Appl. No.: 14/267,753

(22) Filed: May 1, 2014

(65) Prior Publication Data

US 2015/0313585 A1 Nov. 5, 2015

(51) Int. Cl.
| A61B 1/32 | (2006.01) |
| A61B 17/02 | (2006.01) |
| A61F 2/46 | (2006.01) |
| A61B 17/60 | (2006.01) |

(52) U.S. Cl.
CPC ............ *A61B 17/0206* (2013.01); *A61B 17/025* (2013.01); *A61B 17/60* (2013.01); *A61F 2/46* (2013.01); *A61F 2/4611* (2013.01); *A61B 2017/0256* (2013.01)

(58) Field of Classification Search
CPC ............. A61B 17/025; A61B 17/0206; A61B 2017/0256; A61F 2/4611
See application file for complete search history.

(56) References Cited

U.S. PATENT DOCUMENTS

| 5,728,046 | A | 3/1998 | Mayer et al. | |
| 8,357,184 | B2 | 1/2013 | Woolley et al. | |
| 8,435,269 | B2 | 5/2013 | Woolley et al. | |
| 8,535,320 | B2 | 9/2013 | Woolley et al. | |
| 8,727,975 | B1* | 5/2014 | Pfabe | A61B 17/0206 600/231 |
| 2003/0149341 | A1 | 8/2003 | Clifton | |
| 2004/0230191 | A1 | 11/2004 | Frey et al. | |
| 2007/0100212 | A1* | 5/2007 | Pimenta | A61B 5/0488 600/210 |
| 2012/0296171 | A1* | 11/2012 | Lovell | A61B 17/0206 600/213 |
| 2016/0074029 | A1* | 3/2016 | O'Connell | A61B 17/0206 600/213 |

* cited by examiner

*Primary Examiner* — Ellen C Hammond
(74) *Attorney, Agent, or Firm* — Baker & McKenzie LLP

(57) ABSTRACT

A retractor-distractor system comprising a frame with slidably coupled superior and inferior arms extending therefrom. The superior arm comprises a superior clamp arm pivotally coupled to a lateral end of the superior arm, a superior ball joint received between the superior clamp arm and the superior arm, and a superior ball joint lock operable to pivot the superior clamp arm proximate to the superior arm, thereby locking the orientation of the superior ball joint. The inferior arm comprises an inferior clamp arm pivotally coupled to a lateral end of the inferior arm, an inferior ball joint received between the inferior clamp arm and the inferior arm, and an inferior ball joint lock operable to pivot the inferior clamp arm proximate to the inferior arm, thereby locking the orientation of the inferior ball joint. The superior and inferior arms are operable to receive a modular blade to retract and distract tissue.

15 Claims, 18 Drawing Sheets

INTEGRATED RETRACTOR-DISTRACTOR SYSTEM FOR USE WITH MODULAR BONE SCREWS

FIELD OF THE INVENTION

The present disclosure relates to retractor and distractor systems for use with screws and more particularly to an integrated retractor-distractor system for use with modular bone screws.

BACKGROUND OF THE INVENTION

The spinal column of bones is highly complex anatomical structure that includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction. The more than 20 discrete bones of an adult human spinal column are anatomically categorized as one of four classifications—cervical, thoracic, lumbar, or sacral—and are coupled together sequentially to one another by a tri-joint complex that consists of an anterior disc and two posterior facet joints. The anterior discs of adjacent bones are cushioned by cartilage spacers referred to as intervertebral discs or vertebrae. The cervical portion of the spine comprises the top of the spine up to the base of the skull and includes the first seven vertebrae. The intermediate 12 bones are thoracic vertebrae, and connect to the lower spine comprising the 5 lumbar vertebrae. The base of the spine comprises sacral bones, including the coccyx. With its complex nature, however, there is also an increased likelihood that surgery may be needed to correct one or more spinal pathologies.

Genetic or developmental irregularities, trauma, chronic stress, tumors, and disease can result in spinal pathologies that either limit this range of motion or threaten critical elements of the nervous system housed within the spinal column. A variety of systems have been disclosed in the art which achieve this immobilization by implanting artificial assemblies in or on the spinal column. Such systems require surgical implantation during a spinal surgery.

During implantation of such systems, retractors and distractors are commonly used. After an incision is made in a patient's skin, a surgeon will normally use a retractor to retract the patient's skin to create a surgical opening. Then, a distractor is normally used to distract two adjacent vertebral bodies to enlarge the disk space so that the surgeon can insert a spinal implant cage. Typically, the retractor and the distractor are two separate instruments, which results in additional instruments that must be purchased prior to surgery, handled during surgery, and cleaned or discarded after surgery.

Therefore, it is desirable, during surgical implantation of spinal devices, to have an integrated retractor-distractor for use with modular bone screws that allows for percutaneous delivery, independent alignment between bone screws, and improved reliability, durability, and ease of installment of said devices.

BRIEF SUMMARY

Disclosed herein is an integrated retractor-distractor system for use with modular bone screws. In an embodiment, the retractor-distractor system comprises a frame. The frame comprises a superior arm and an inferior arm, each slidably coupled to and extending from the frame. The frame is operable to slide the superior arm and the inferior arm in both superior and inferior directions relative to the frame.

The superior arm may further comprise a superior clamp arm pivotally coupled to a lateral end of the superior arm, a superior ball joint received between the superior clamp arm and the superior arm, and a superior ball joint lock operable to pivot the superior clamp arm proximate to the superior arm, thereby locking the orientation of the superior ball joint. The superior arm, the superior clamp arm, and the superior ball joint each comprise an opening within their respective inferior sides, the openings operable to receive a modular blade operable to retract and distract tissue.

The inferior arm may further comprise an inferior clamp arm pivotally coupled to a lateral end of the inferior arm, an inferior ball joint received between the inferior clamp arm and the inferior arm, and an inferior ball joint lock operable to pivot the inferior clamp arm proximate to the inferior arm, thereby locking the orientation of the inferior ball joint. The inferior arm, the inferior clamp arm, and the inferior ball joint each comprise an opening within their respective superior sides, the openings operable to receive a modular blade operable to retract and distract tissue.

In an embodiment, the retractor-distractor system comprises a modular blade. The blade comprises a distal end and a proximal end, a ball joint connecting shaft proximate to the proximal end, a retractor skin extending from the ball joint connecting shaft to the distal end, and a clamping mechanism proximate to the distal end. The clamping mechanism may be operable to releasably attach to a modular bone screw. The modular blade may be operable to be removably attached to the frame in the retractor-distractor system. The retractor skin may be operable to retract and distract tissue.

BRIEF DESCRIPTION OF THE DRAWINGS

Embodiments are illustrated by way of example in the accompanying figures, in which like reference numbers indicate similar parts, and in which.

DETAILED DESCRIPTION

In the embodiments described below, various components are defined in relation to each other using the positional terms of superior/inferior, medial/lateral, and distal/proximal. In operation and while used during spinal surgery, "superior" refers to closer to the head, while "inferior" refers to closer to the feet. "Medial" refers to closer to the midline (spine) of the body, while "lateral" refers to away from the midline of the body. "Proximal" refers to closer to the user/surgeon, while "distal" refers to away from the user/surgeon. It is to be understood that the superior/inferior designations on various components may be used interchangeably depending on whether the surgeon performs surgery on the spine while standing proximate to the left side of the patient's body or proximate to the right side of the patient's body as long as the superior direction is closer to the patient's head.

Figure 1:
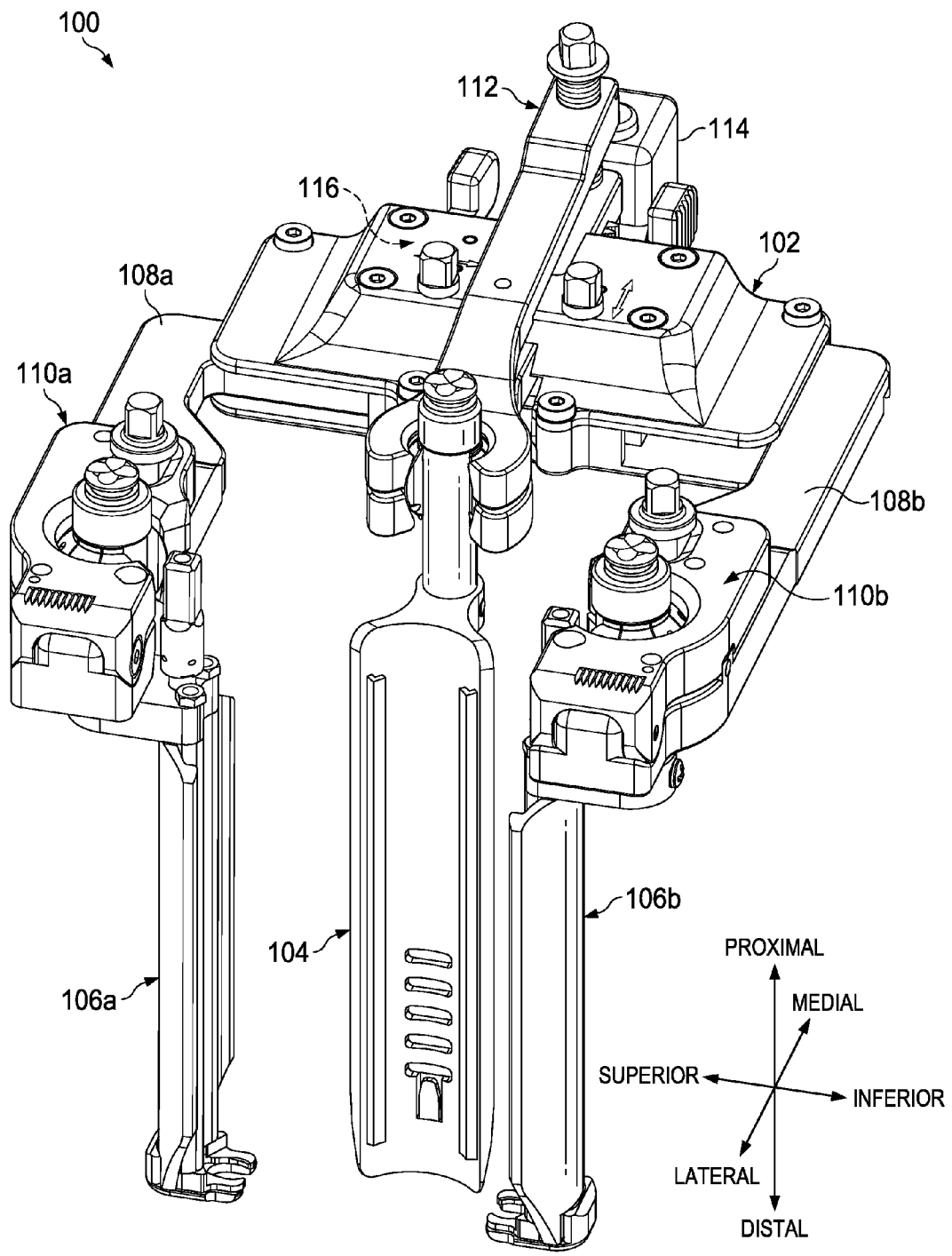
FIG. 1 depicts a perspective view of an integrated retractor-distractor system, in accordance with one embodiment of the present disclosure.

FIG. 1 depicts a perspective view of an integrated retractor-distractor system 100, in accordance with one embodiment of the present disclosure. The integrated retractor-distractor system 100 comprises a frame 102, a modular medial blade 104, a first modular superior/inferior blade 106a removably connected to a first superior/inferior sliding arm 108a and a first superior/inferior arm clamp 110a, and a second modular superior/inferior blade 106b removably connected to a second superior/inferior sliding arm 108b and a second superior/inferior arm clamp 110b. The first and second superior/inferior slidable arms 108a, 108b may be L-shaped and may be operable to translate (slide) in both superior and inferior directions relative to each other at a gearing system 116 (internal, not shown). The frame 102 may further comprise a pivot arm 112.

The integrated retractor-distractor system 100 may be operable to rigidly affix to a patient bedframe (not shown) at a tail frame 114. The tail frame may be connected to a rigid arm (not shown) connected to a bedframe rail (not shown) or may be connected directly to the bedframe rail.

Figure 2:
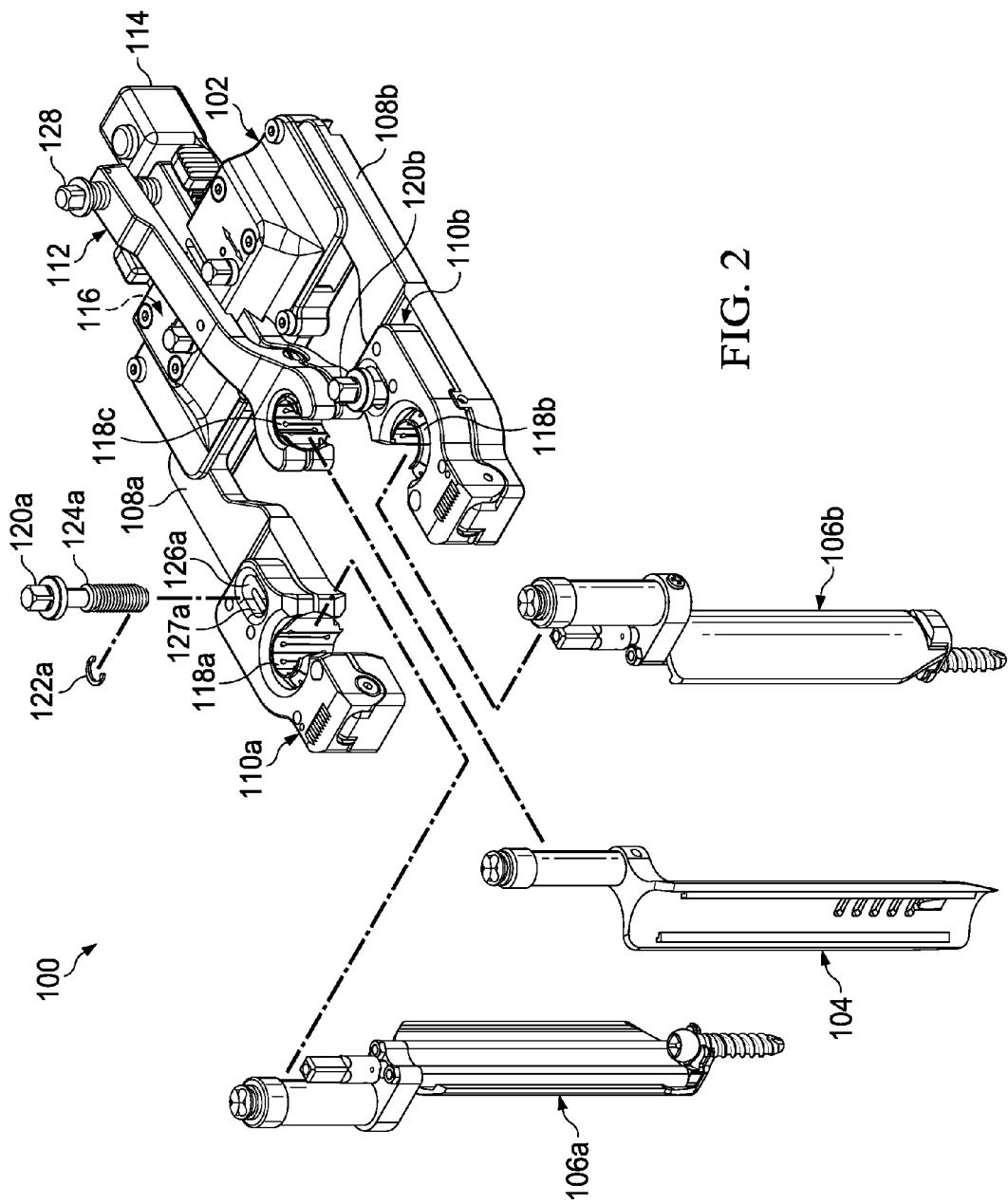
FIG. 2 depicts an exploded perspective view of the integrated retractor-distractor system of FIG. 1, in accordance with one embodiment of the present disclosure.

FIG. 2 depicts an exploded perspective view of the integrated retractor-distractor system 100 of FIG. 1, in accordance with one embodiment of the present disclosure. As depicted in FIG. 2, the first blade 106a may be received within a first ball joint 118a at an opening. The first ball joint 118a may be received within openings in the first arm clamp 110a of the first sliding arm 108a. The second blade 106b may be received within a second ball joint 118b at an opening. The second ball joint 118a may be received within openings in the second arm clamp 110b of the second sliding arm 108b. The first and second blades 106a, 106b may be locked within the first and second ball joints 118a, 118b with the first and second ball joint locks 120a, 120b, respectively.

Each of the first and second ball joint locks 120a, 120b may comprise a screw-like shape, including a head at a proximal end and a shaft at a proximal end. The shaft may comprise a threaded portion opposite the head and each threaded portion may be operable to be threaded through non-threaded apertures 126a, 126b defined through the first and second arm clamps 110a, 110b and into and mate with threaded apertures (not shown) defined in the first and second sliding arms 108a, 108b. When received within and through the first and second arm clamps 110a, 110b and the first and second sliding arms 108a, 108b, the first and second ball joint locks 120a, 120b may extend through and beyond a proximal, lower surface of the first and second sliding arms 108a, 108b. The apertures 126a, 126b in the first and second arm clamps 110a, 110b may be substantially oval in shape, allowing the first and second arm clamps 110a, 110b to pivot relative to the first and second sliding arms 108a, 108b and the first and second ball joint locks 120a, 120b when the first and second ball joint locks 120a, 120b are received therethrough. The apertures 126a, 126b may further comprise aperture shoulders 127a, 127b (not shown) within the apertures that are operable to interact with the first and second ball joint locks 120a, 120b, as discussed below.

As shown relative to first sliding arm 108a, at a proximal end of the first ball joint lock 120a, a burr 122a may be attached to the ball joint lock 120a, thereby preventing the ball joint lock 120a from being entirely removed from the first arm clamp 110a and the first sliding arm 108a. The burr 122a may be a removable clip, a soldered bead, or any other burr with a diameter larger than a diameter of the aperture in the first sliding arms 108a so that the burr 122a cannot be threaded through the threaded aperture.

Also shown relative to the first sliding arm 108a, the first ball joint lock 120a may comprise a lifting shoulder 124a positioned approximately halfway about the shaft of the first ball joint lock 120a. The lifting shoulder 124a may have a diameter larger than a diameter of the aperture 126a at the aperture shoulder 127a so that the first ball joint lock 120a cannot be removed through the aperture 126a in the first arm clamp 110a.

In operation, the lifting shoulder 124a may be positioned between the aperture 126a in the first arm clamp 110a and the threaded aperture in the first sliding arm 108a so that when the first ball joint lock 120a is rotated counter-clockwise, the lifting shoulder 124a interacts with the aperture shoulder 127a and causes the first arm clamp 110a to pivot upwardly.

The upward pivot causes the first arm clamp 110a to be loosened about the first ball joint 118a, thereby allowing the first blade 106a multiple degrees of freedom, in both rotation and translation, as discussed later. When the first ball joint lock 120a is rotated clockwise, the head of the first ball joint lock 120a interacts with an upper surface of the first arm clamp 110a and causes the first arm clamp 110a to pivot downwardly. The downward pivot causes the first arm clamp 110b to be tightened about the first ball joint 118, locking the orientation of the first blade 106a.

Although not shown, the burr 122a and the lifting shoulder 124a of the first ball joint lock 120a and the aperture shoulder 127a are also present on the second ball joint lock 120b and the second aperture 126b, respectively. The second blade 106b, the second sliding arm 108b, the second arm clamp 110b, the second ball joint 118b, and the second ball joint lock 120b operate similarly to respective components 106a, 108a, 110a, 118a, and 120a.

The integrated retractor-distractor system 100 may further comprise a third ball joint 118c operable to receive the medial blade 104 at an opening. The third ball joint 118c may be received within the pivot arm 112. The pivot arm 112 may be tightened or loosened about the third ball joint 118c with a pivot locking screw 128. When the pivot locking screw 128 is rotated counter-clockwise, a medial end of the pivot arm 112 is lowered, loosening the third ball joint 118c and allowing the medial blade 104 multiple degrees of freedom, in both rotation and translation, as discussed later. When the pivot locking screw 128 is rotated clockwise, the medial end of the pivot locking arm 112 is raised, tightening the ball joint 118c and locking the medial blade 104 in place.

Figure 3A:
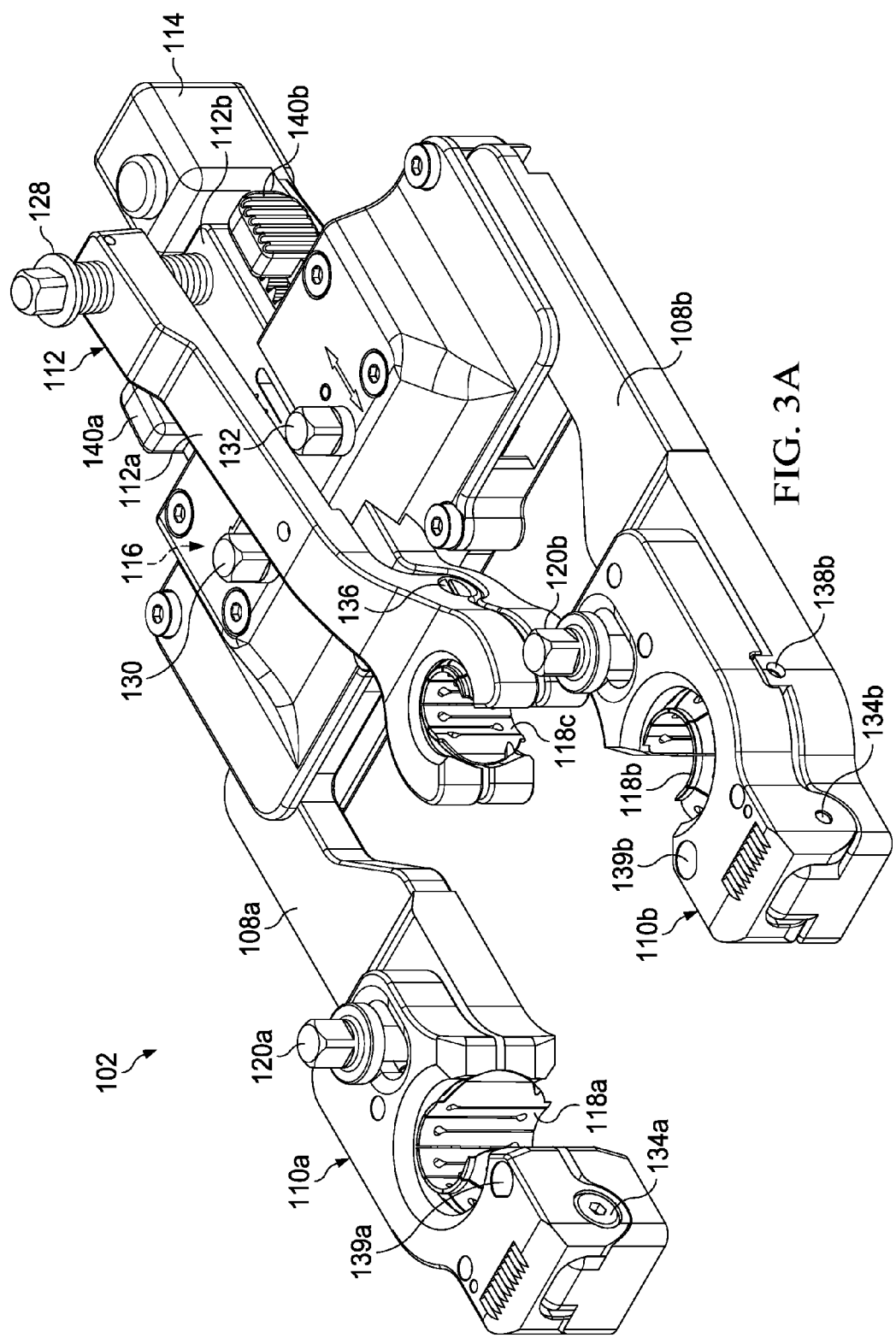
FIG. 3A depicts a perspective view of a frame of the integrated retractor-distractor system of FIGS. 1 and 2, in accordance with one embodiment of the present disclosure.

FIG. 3A depicts a perspective view of the frame 102 of the integrated retractor-distractor system of FIGS. 1 and 2, in accordance with one embodiment of the present disclosure. In addition to the elements described and related to FIGS. 1 and 2, the gearing mechanism 116 of the frame 102 further comprises a superior/inferior gearing drive 130 operable to adjust the width of the superior/inferior sliding arms 108a, 108b, and a lateral/medial gearing drive 132 operable to adjust the lateral/medial position of the pivot arm 112.

In operation, the superior/inferior sliding arms 108a, 108b may be moved closer to each other when the surgeon squeezes tabs 140a, 140b and rotates the superior/inferior gearing drive 130 in a counter-clockwise direction with a removable driver (not shown). The superior/inferior sliding arms 108a, 108b may be moved apart from each other when the surgeon rotates the superior/inferior gearing drive 130 in a clockwise direction with a removable driver (not shown). Likewise, the pivot arm 112 may be moved in a medial direction closer to the tail frame 114 when the surgeon squeezes the tabs 140a, 140b and rotates the lateral/medial gearing drive 132 in a clockwise direction with a removable driver (not shown) and may be moved in a lateral direction away from the tail frame 114 when the surgeon squeezes the tabs 140a, 140b and rotates the lateral/medial gearing drive 132 in a counter-clockwise direction with a removable driver (not shown).

FIG. 3A additionally depicts sliding arm pivot pins 134a, 134b connecting arm clamps 110a, 110b to sliding arms 108a, 108b. The pivot pins 134a, 134b may be located proximate to ends of the arm clamps 110a, 110b and ends of the sliding arms 108a, 108b, thereby allowing the arm clamps 110a, 110b to pivot upwardly relative to the sliding arms 108a, 108b. By allowing the arm clamps 110a, 110b to pivot, the ball joints 118a, 118b may be compressed when the ball joint locks 120a, 120b are rotated clockwise in order to lock superior/inferior blades (not shown) in place, or may be released when the ball joint locks 120a, 120b are rotated counter-clockwise in order to allow superior/inferior blades to be removed from the frame 102 or independently rotated/translated relative to the frame 102.

In an embodiment, the frame 102 may further comprises a pivot arm pivot pin 136 that connects two parts of pivot arm 112 to each other. Upper pivot arm 112a and lower pivot arm 112b may be operable to pivot relative to each other at the pivot arm pivot pin 136. The pivot arm pivot pin 136 may be located on the frame 102 side of the ball joint 118c and proximate to the ball joint 118c. By allowing the upper pivot arm 112a to pivot relative to the lower pivot arm 112b, the ball joint 118c may be compressed when the pivot locking screw 128 is rotated clockwise in order to lock the medial blade (not shown) in place, or may be released when the pivot locking screw 128 is rotated counter-clockwise in order to allow the medial blade to be removed from the frame 102 or rotated/translated relative to the frame 102. The pivot arm pivot pin 136 also allows the upper pivot arm 112a and the lower pivot arm 112b to move in unison relative to the frame 102 in both medial and lateral directions when the surgeon adjusts the position of the pivot arm 112 with the lateral/medial gearing drive 132.

The sliding arm 108b may further comprise a ball joint locking pin 138b that is operable to extend into a center slot (not shown) in the ball joint 118b. As discussed below, the ball joint locking pin 138b ensures that the opening of the ball joint 118b remains aligned with the openings in the sliding arm 108b and the arm clamp 110b, allowing the superior/inferior blade 106b to be attached to or removed from the frame 102 during surgery. Although not shown, the sliding arm 108a and the lower pivot arm 112b additionally comprise ball joint locking pins that extend into center slots of ball joints 118a, 118c, respectively. These ball joint locking pins similarly ensure that the openings of the ball joints 118a, 118c remain aligned with openings in the sliding arm 108a, the arm claim 110a, the upper pivot arm 112a, and the lower pivot arm 112b.

The arm clamps 110a, 110b may further comprise instrument apertures 139a, 139b that may be located between the ball joints 118a, 118b and the sliding arm pivot pins 134a, 134b and that may be operable to receive an add-on surgical accessory or instrument such as surgical lighting.

Figure 3B:
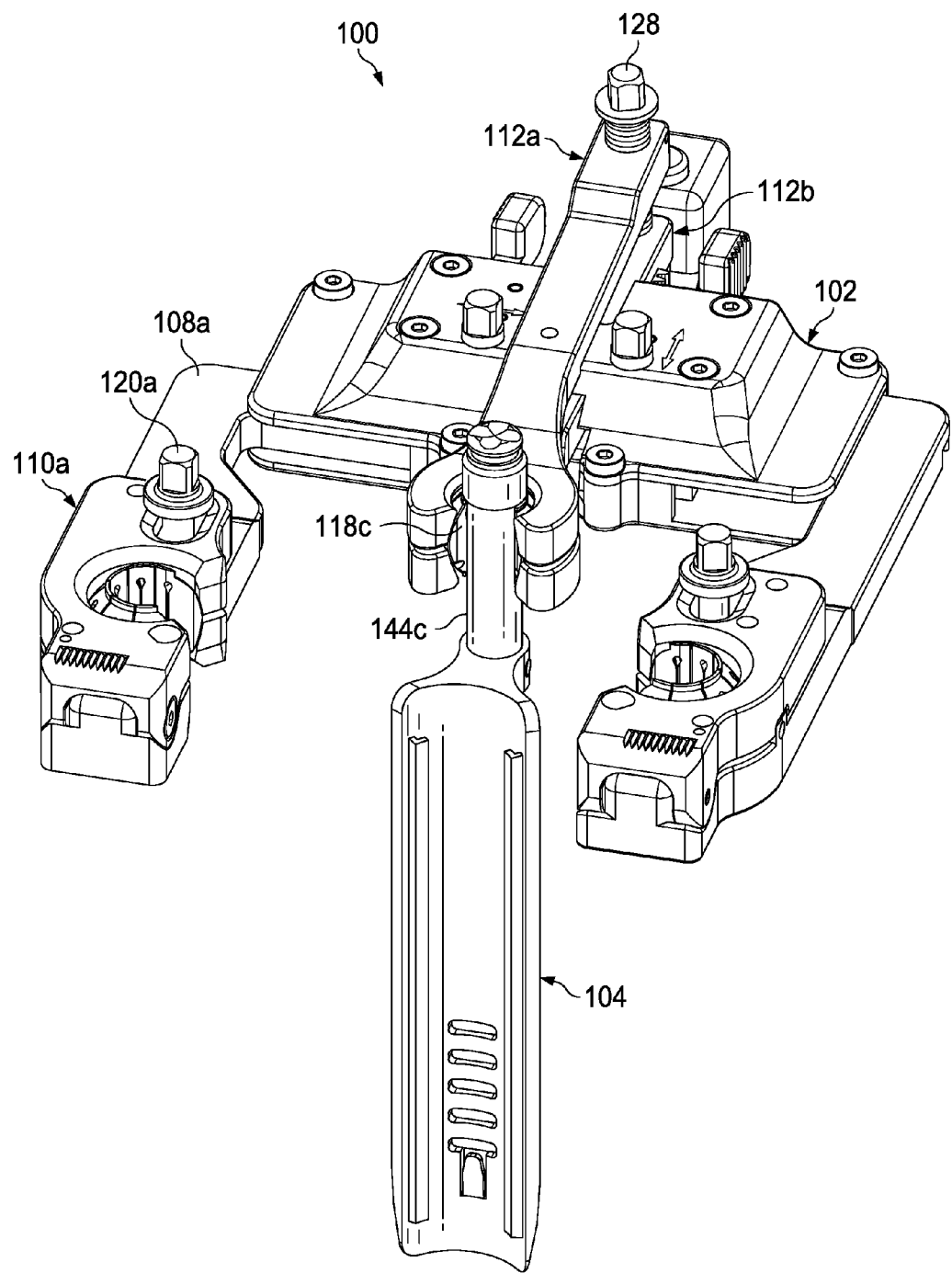
FIG. 3B depicts a perspective view of the frame of the integrated retractor-distractor system of FIG. 3A with a modular medial blade removably attached, in accordance with one embodiment of the present disclosure.
Figure 3C:
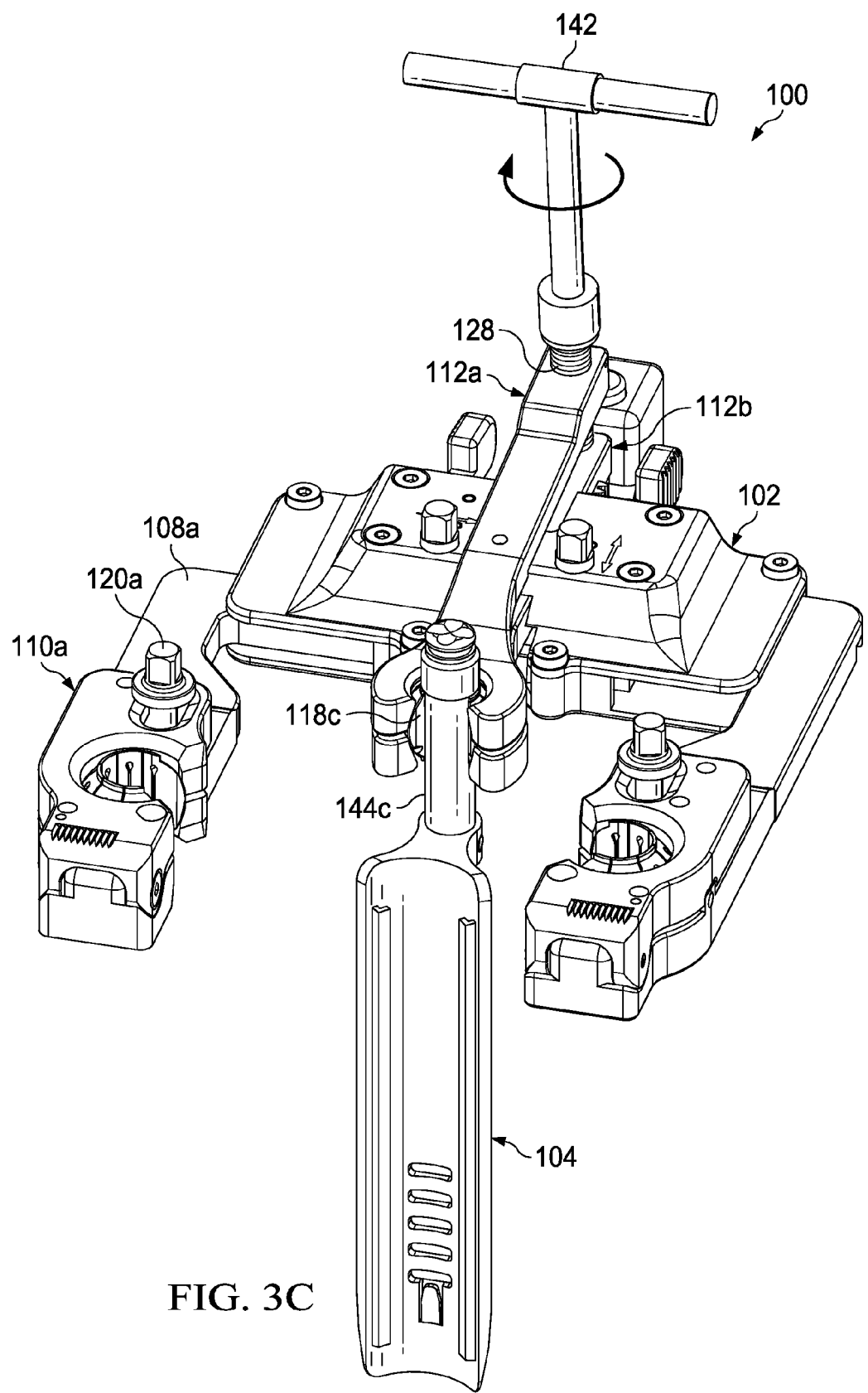
FIG. 3C depicts a perspective view of the frame and the medial blade of the integrated retractor-distractor system of FIG. 3B with a driver attached, in accordance with one embodiment of the present disclosure.

FIG. 3B depicts a perspective view of the frame of the integrated retractor-distractor system 100 of FIG. 3A with the modular medial blade 104 removably attached, in accordance with one embodiment of the present disclosure. FIG. 3C depicts a perspective view of the frame 102 and the modular medial blade 104 of the integrated retractor-distractor system of FIG. 3B with a driver 142 attached, in accordance with one embodiment of the present disclosure.

As shown in FIG. 3B, when the upper pivot arm 112a is in a lowered position proximate to lower pivot arm 112b and the ball joint 118c is not compressed, the medial blade 104 may be attached to the frame 102 within the ball joint 118c when openings in the ball joint 118c and upper and lower pivot arms 112a, 112b are each aligned. In this position, the medial blade 104 may be "snapped" into the ball joint 118c and has multiple degrees of freedom relative to the frame 102. The medial blade 104 may translate proximally or distally approximately 10 mm about a medial blade ball joint connection shaft 144 and may rotate in three degrees of freedom.

As shown in FIG. 3C, when the medial blade 104 is placed in its desired position, a removable driver 142 may be used to rotate the pivot locking screw 128 in a clockwise rotation. When the pivot locking screw 128 is rotated in a clockwise rotation, the upper pivot arm 112a climbs the threads of the pivot locking screw 128, thereby clamping the ball joint 118c against the medial blade ball joint connection shaft 144 and locking the medial blade 104 in its desired position relative to the frame 102.

Figure 3D:
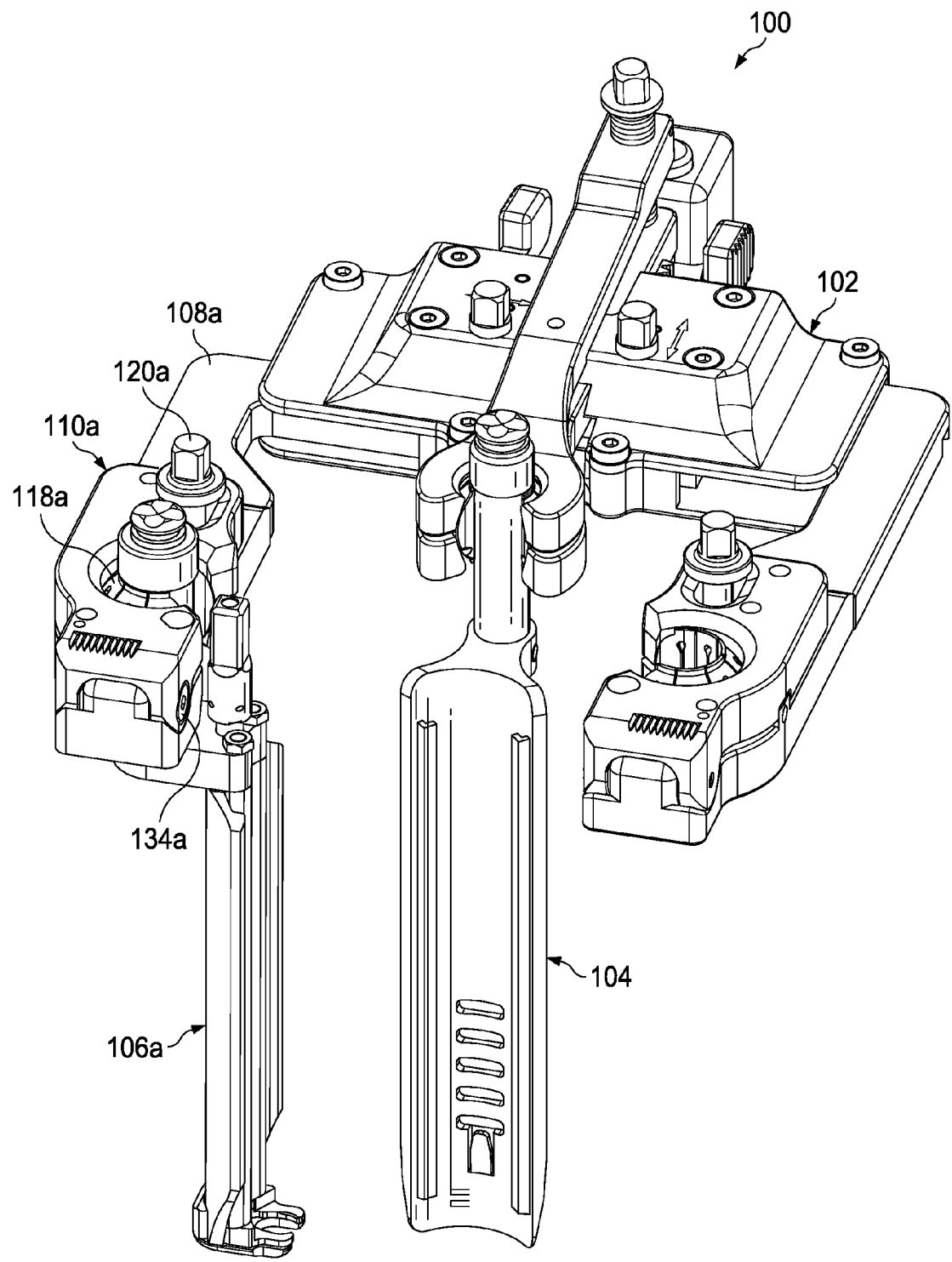
FIG. 3D depicts a perspective view of the frame and the medial blade of the integrated retractor-distractor system of FIG. 3B with a modular superior blade removably attached, in accordance with one embodiment of the present disclosure.
Figure 3E:
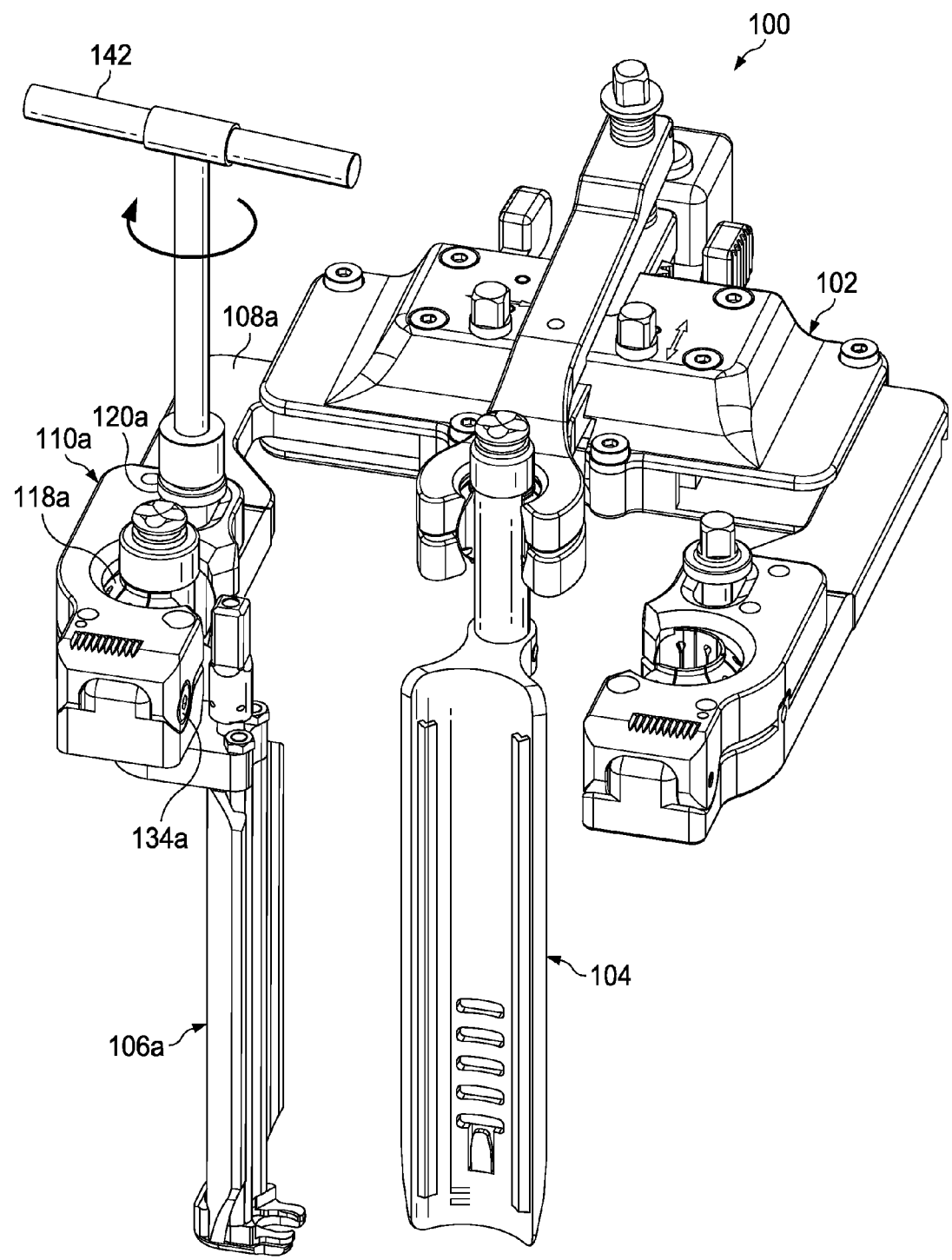
FIG. 3E depicts a perspective view of the frame, the modular medial blade, and the modular superior blade of the integrated retractor-distractor system of FIG. 3D with a driver attached, in accordance with one embodiment of the present disclosure.

FIG. 3D depicts a perspective view of the frame 102 and the modular medial blade 104 of the integrated retractor-distractor system 100 of FIG. 3B with a superior blade 106a removably attached, in accordance with one embodiment of the present disclosure. FIG. 3E depicts a perspective view of the frame 102, the modular medial blade 104, and the modular superior blade 106a of the integrated retractor-distractor system 100 of FIG. 3D with the driver 142 attached, in accordance with one embodiment of the present disclosure.

As shown in FIG. 3D, when the arm clamp 110a is in a raised position, the superior blade 106a may be attached to the frame 102 within the ball joint 118a when openings in the ball joint 118a, the superior sliding arm 108a, and the superior arm clamp 110a are each aligned. In this position, the superior blade 106a may be "snapped" into the ball joint 118a and has multiple degrees of freedom relative to the frame 102. The superior blade 106a may translate proximally or distally approximately 10 mm about a superior blade connection shaft (not shown) and may rotate in three degrees of freedom.

As shown in FIG. 3E, when the superior blade 106a is placed in its desired position, the removable driver 142 may be used to rotate the superior ball joint lock 120a in a clockwise rotation. When the superior ball joint lock 120a is rotated in a clockwise rotation, the superior arm clamp 110a may be driven downwards towards the superior sliding arm 108a, thereby clamping the ball joint 118a against the superior blade ball joint connection shaft 144a, locking the superior blade 106a in its desired position relative to the frame 102.

Although not shown in FIG. 3E, an inferior superior blade is operable to function identically to the superior blade 106a.

Figure 4A:
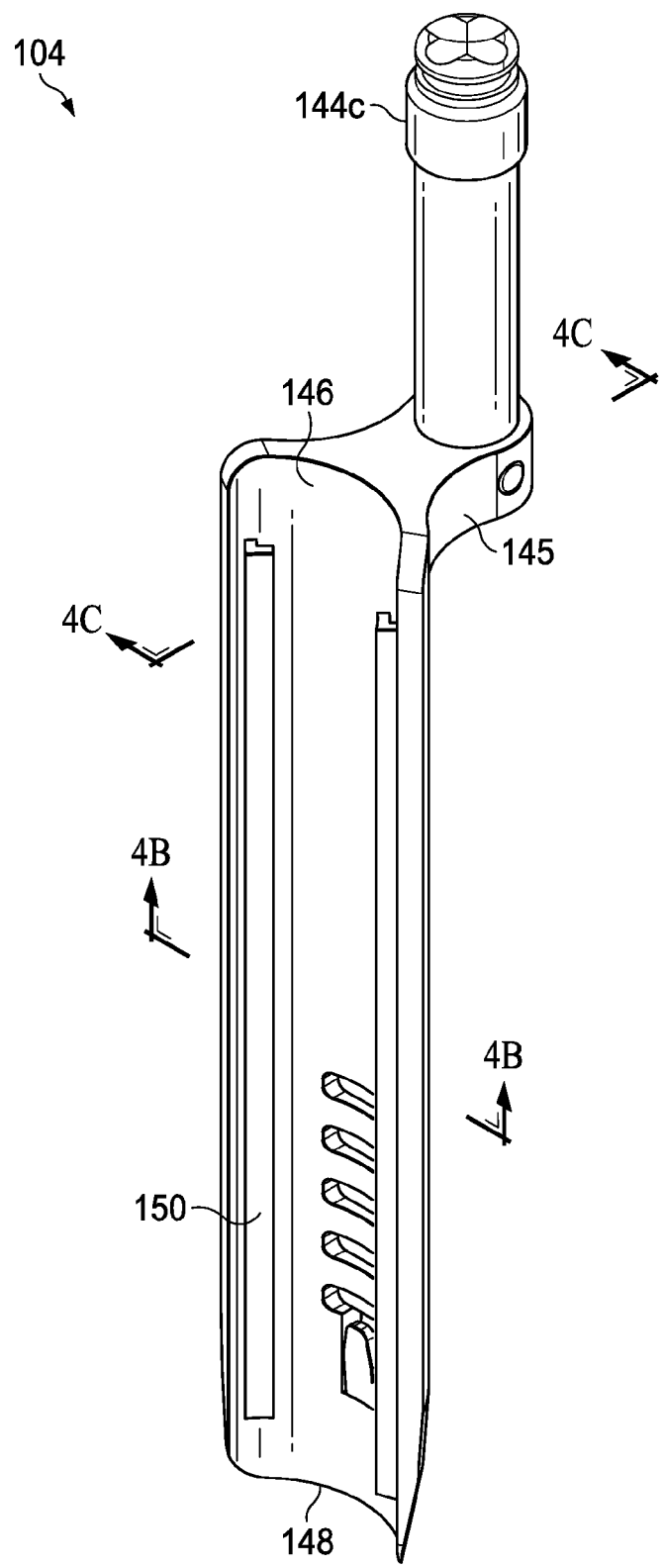
FIG. 4A depicts a perspective view of a modular medial blade of the integrated retractor-distractor system of FIG. 1, in accordance with one embodiment of the present disclosure.

FIG. 4A depicts a perspective view of the modular medial blade 104 of the integrated retractor-distractor system of FIG. 1, in accordance with one embodiment of the present disclosure. The medial blade 104 comprises the ball joint connection shaft 144 at a proximal end that is operable to be received within a ball joint (not shown), a shoulder 145, and a retractor skin 146. The retractor skin 146 may be offset from the ball joint connection shaft 144 by the shoulder 145 and may curve outwardly from the shoulder 145 substantially entirely the length of the retractor skin 146. The retractor skin 146 may extend from the shoulder 145 to a distal end at a blade edge 148. The blade edge 148 may be used to clean a pedicle or scrape tissue on a bone at the surgical site. The retractor skin 146 may further comprise internal rails 150 operable to receive a modular tool, such as a removable light.

Figure 4B:
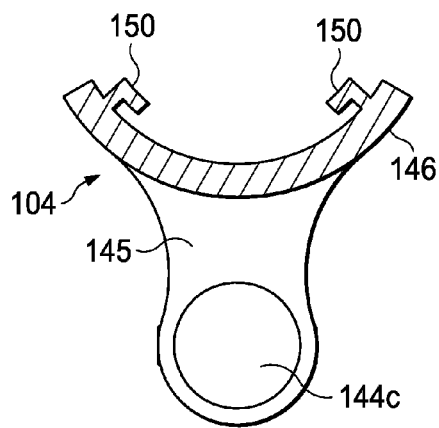
FIG. 4B depicts a sectional view of the modular medial blade of FIG. 4A, in accordance with one embodiment of the present disclosure.
Figure 4C:
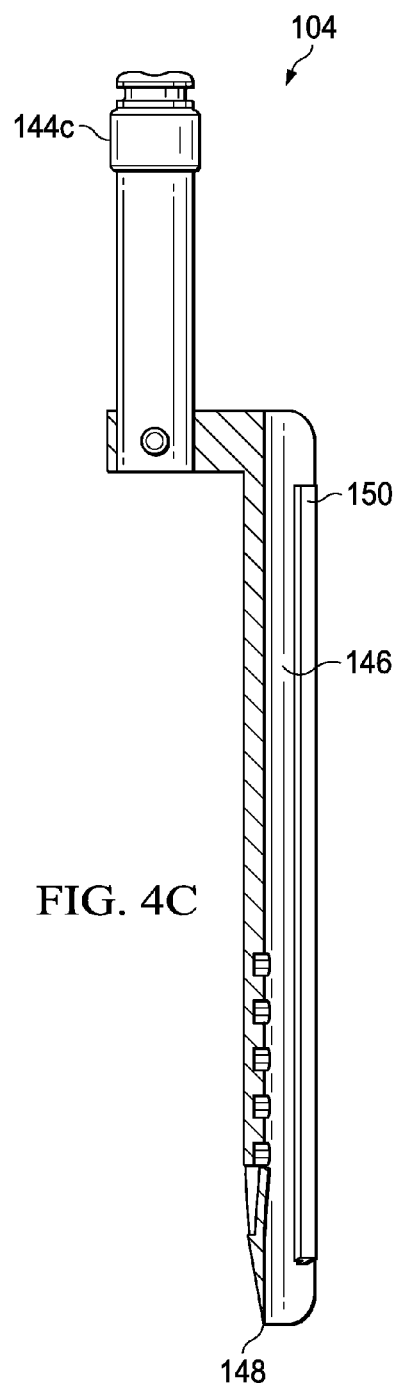
FIG. 4C depicts a sectional view of the modular medial blade of FIG. 4B, in accordance with one embodiment of the present disclosure.

FIG. 4B depicts a sectional view of the modular medial blade 104 of FIG. 4A, in accordance with one embodiment of the present disclosure. FIG. 4C depicts a sectional view of the modular medial blade 104 of FIG. 4B, in accordance with one embodiment of the present disclosure. FIG. 4B depicts the curvature of the retractor skin 146 away from the ball joint connection shaft 144, the shoulder 145, and the location of the internal rails 150 proximate to edges of the retractor skin 146. FIG. 4C depicts a profile of the medial blade 104 with the ball joint connection shaft 144 at a proximal end extending to the shoulder 145 and the retractor skin 146 and ending at the blade edge 148 at a proximal end.

Figure 5A:
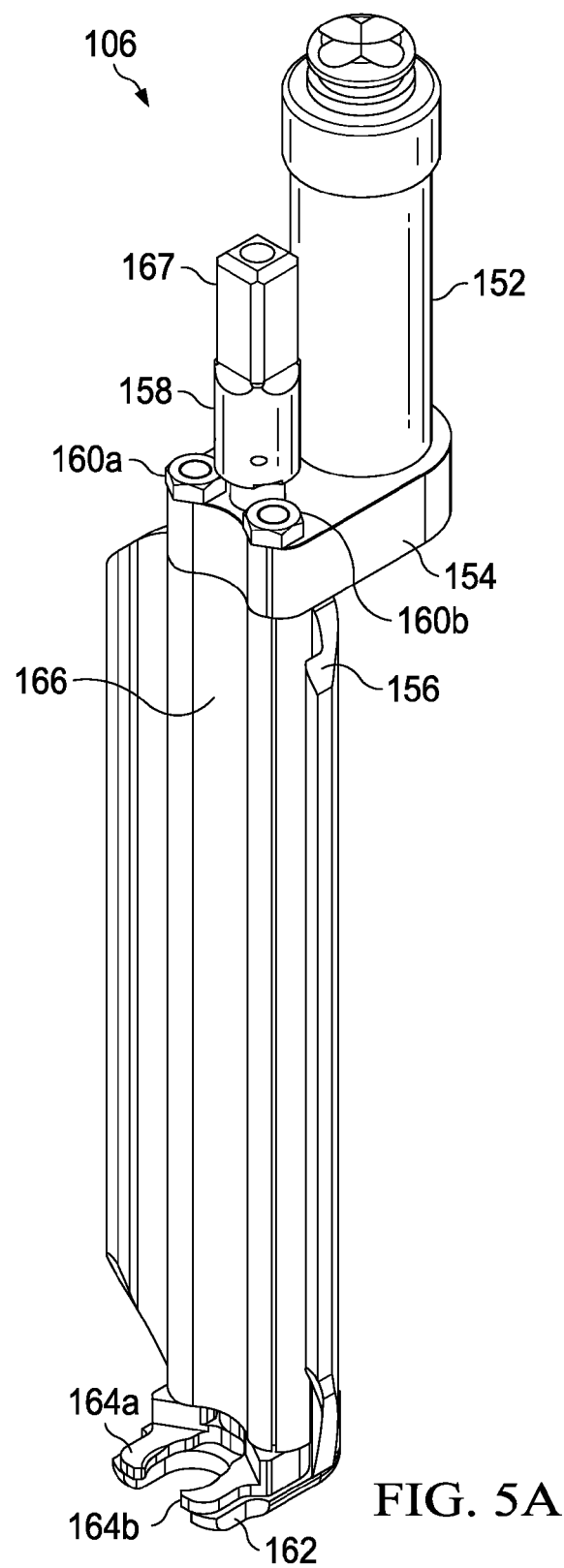
FIG. 5A depicts a perspective view of a modular superior/inferior blade of the integrate retractor-distractor system of FIG. 1, in accordance with one embodiment of the present disclosure.

FIG. 5A depicts a perspective view of a modular superior/inferior blade 106 of the integrated retractor-distractor system 100 of FIG. 1, in accordance with one embodiment of the present disclosure. The blade 106 may be either the superior blade 106a or the inferior blade 106b, as depicted in FIG. 1, as both blades have identical features and may be used interchangeably.

The blade 106 may comprise a ball joint connection shaft 152 located at a proximal end of the blade that is operable to be received within a ball joint (not shown), a shoulder 154, and a retractor skin 156. The retractor skin 156 may be offset from the ball joint connection shaft 152 by the shoulder 154 and may curve outwardly from the shoulder 154 substantially the entire length of the retractor skin 156. The retractor skin 156 may extend from the shoulder 154 to a distal end at a shoe base 162. The blade 106 may translate proximally or distally approximately 10 mm about the ball joint connection shaft 152 and may rotate in three degrees of freedom.

The blade 106 may further comprise a clamping mechanism comprising a locking rod 158, left and right pivoting pins 160a, 160b, left and right clamps 164a, 164b, and a clamping mechanism encasement 166. The locking rod 158 and the left and right pivoting pins 160a, 160b may extend within apertures (not shown) in the clamping mechanism encasement 166 from the shoulder 154 to the shoe base 162. The locking rod 158 may be located proximate to the ball joint connecting shaft 152 and may comprise a locking rod head 167 above the shoulder 154 that is operable to be rotated by the driver (not shown) discussed previously. The left and right pivoting pins 160a, 160b are located outside of the locking rod 158 and extend from the shoulder 152 through apertures in the left and right clamps 164a, 164b to the shoe base 162. The left and right clamps 164a, 164b are operable to pivot relative to the shoe base 162 between open and closed positions. Like the retractor skin 156, the clamping mechanism encasement 166 may be curved with a curvature that matches that of a bone screw driver (discussed below). The retractor skin 156 and the clamping mechanism encasement 166 may be manufactured as a single part or separate parts.

Figure 5B:
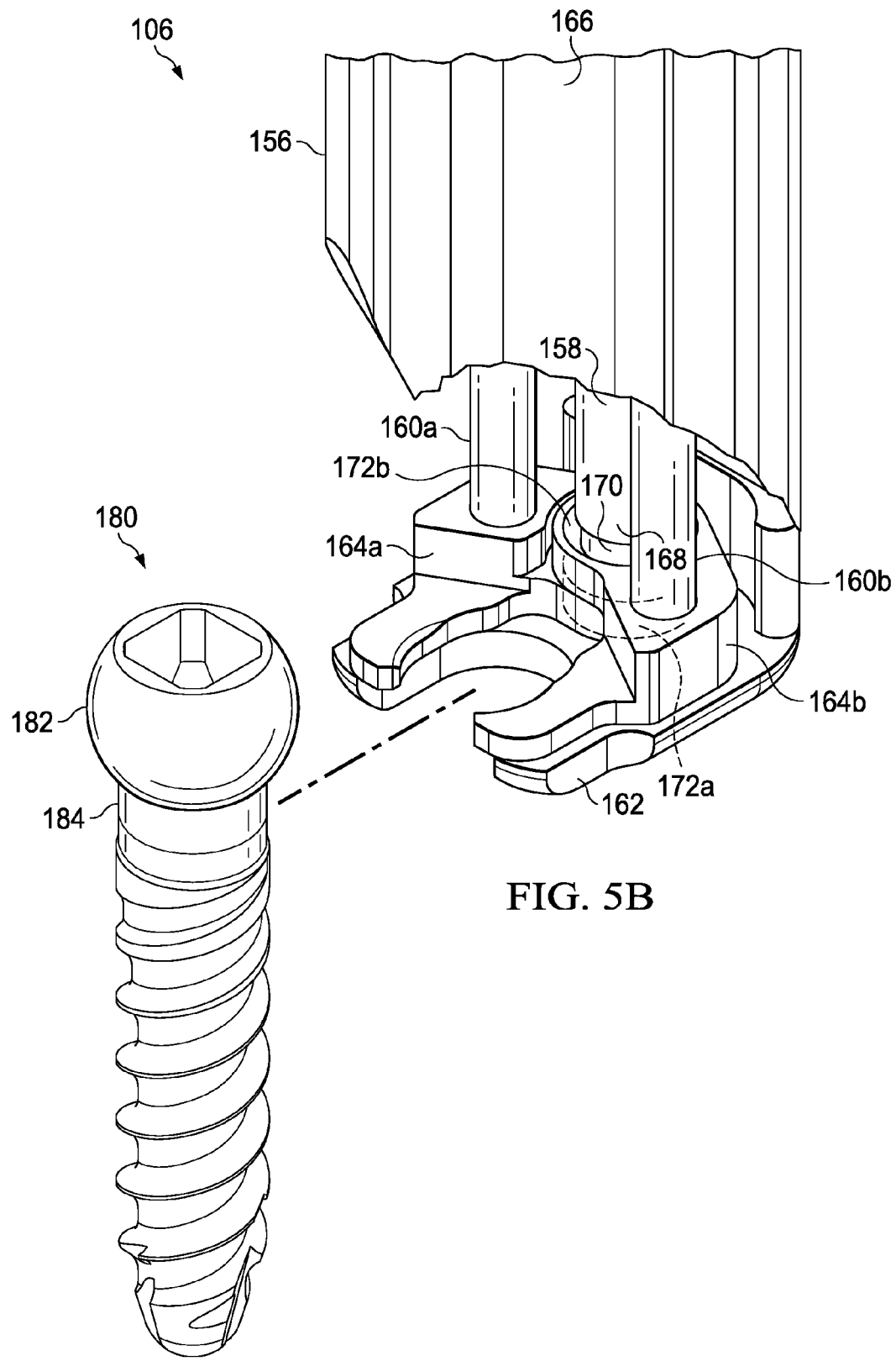
FIG. 5B depicts a partial cutaway view of a clamping mechanism of the modular superior/inferior blade of FIG. 5A with a modular bone screw, in accordance with one embodiment of the present disclosure.

FIG. 5B depicts a partial cutaway view of a clamping mechanism of the modular superior/inferior blade 106 of FIG. 5A with a modular bone screw 180, in accordance with one embodiment of the present disclosure. As depicted in FIG. 5B, part of the retractor skin 156 and the clamping mechanism encasement 166 have been cut away to depict the internal workings of the clamping mechanism. The left and right clamps 164a, 164b may be curved to fit around a shaft of a bone screw in the closed position.

The locking rod 158 may comprise a two part system with an internal locking rod 170 received within an internal aperture of an external locking rod 168. The external locking rod 168 may comprise a first diameter while the internal locking rod 170 comprises a second, smaller diameter. Both the left and the right clamps 164a, 164b comprise an aperture 172a (not shown), 172b extending therethrough and operable to receive the locking rod 158. The apertures 172a, 172b are sized to receive both the internal locking rod 170 and the external locking rod 168.

The external locking rod 168 is operable to rotate about the internal locking rod 170 when the locking rod head 167 of the locking rod 160 is rotated counter-clockwise and loosened. When the external locking rod 168 is withdrawn from the apertures 172a, 172b of the left and right clamps 164a, 164b, the internal locking rod 170 remains within the apertures 172a, 172b. Because the internal locking rod 170 has a smaller diameter than the external locking rod 168 and the apertures 172a, 172b, the left and right clamps 164a, 164 are operable to pivot above the shoe base 162 when the external locking rod 168 is withdrawn from the apertures 172a, 172b. However, because the internal locking rod 170 is still received within the apertures 172a, 172b, the range of motion that the left and right clamps 164a, 164b may pivot is limited by the internal locking rod 170.

The shoe base 162 comprises an opening that allows the shoe base 162 to be received around a shaft 184 of the bone screw 180, but a diameter of a head 182 of the bone screw 182 is larger than the opening of the shoe base 162, preventing the superior/inferior blade 106 from being removed from the bone screw 180 over the head 182 of the bone screw 180.

In operation, the locking rod 157 may be rotated counterclockwise with a removable driver (not shown), thereby withdrawing the external locking rod 168 from the apertures 172a, 172b of the left and right clamps 164a, 164b. This allows the left and right clamps 164a, 164b to both pivot to an open position wherein the clamps open as wide as or wider than the opening defined by the shoe base 162. The blade 106 may then be received around the bone screw 180 at the bone screw shaft 184 and proximal to the bone screw head 182. The diameter of the opening of the shoe base 162 is sized to be great than a diameter of the bone screw shaft 184, thereby allowing the bone screw 180 to pivot and rotate within the shoe base 162.

After the bone screw 180 has been received within the shoe base 162 and the left and right clamps 164a, 164b, the left and right clamps 164a, 164b may be tightened about the bone screw shaft 184, clamping the bone screw 180 to the blade 106 while still allowing the bone screw 180 to pivot and rotate relative to the blade 106.

When the locking rod head 167 is rotated clockwise by the removable driver (not shown), the external locking rod 168 is driven downwardly over the internal locking rod 170. The larger diameter of the external locking rod 168 self-centers the apertures 172a, 172b of the left and right clamps 164a, 164b, causing the left and right clamps 164a, 164b to both pivot inwardly and around the bone screw shaft 184. When the external locking rod 168 is received within the apertures 172a, 172b of the left and right clamps 164a, 164b, the left and right clamps 164a, 164b can no longer pivot and the bone screw 180 is locked within the blade 106.

Figure 5C:
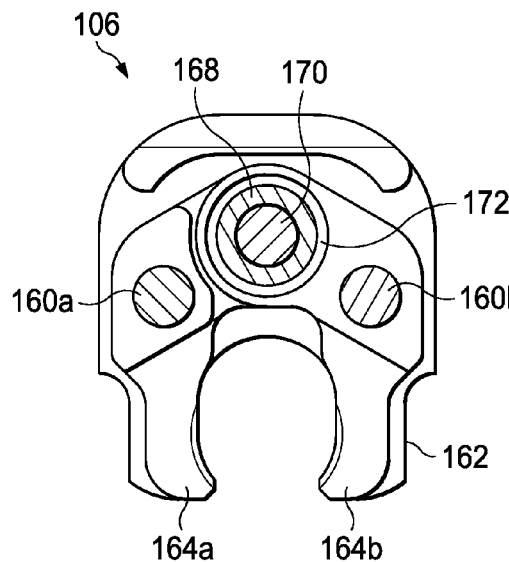
FIGS. 5C-5F depict partial views of the clamping mechanism of the modular superior/inferior blade of FIG. 5B in various positions clamped around the modular bone screw, in accordance with one embodiment of the present disclosure.
Figure 5E:
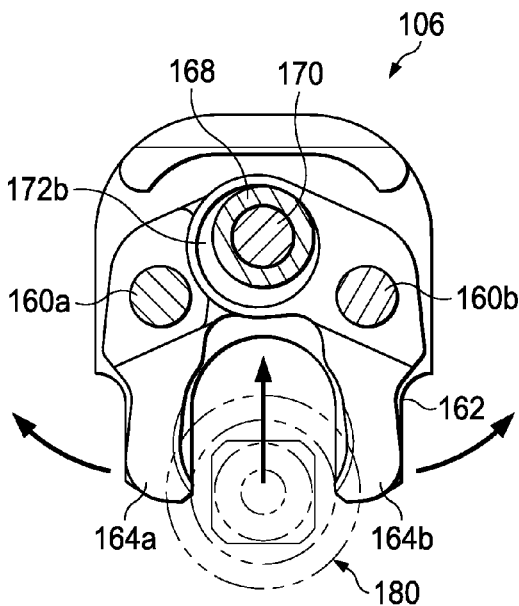
Figure 5D:
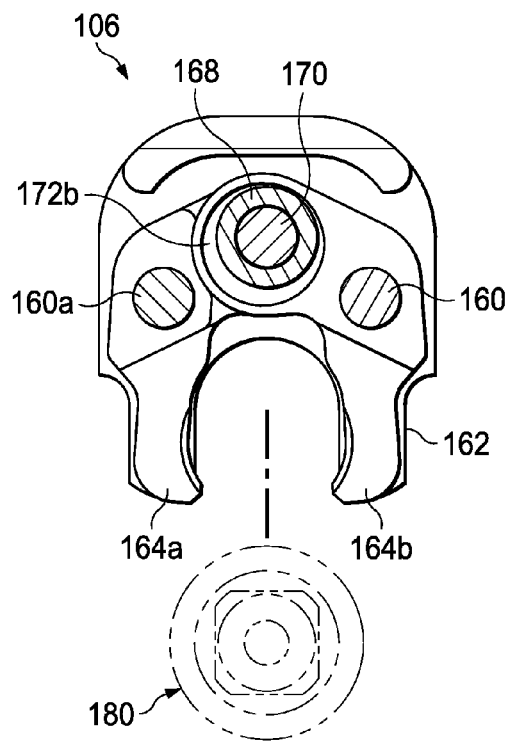
Figure 5F:
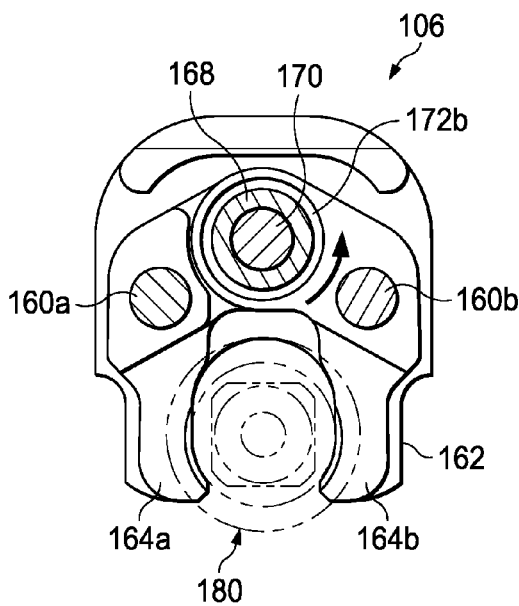

FIG. 5C, FIG. 5D, FIG. 5E, and FIG. 5F depict partial views of the clamping mechanism of the modular superior/inferior blade 106 of FIG. 5B in various positions clamped around the modular bone screw 180, in accordance with one embodiment of the present disclosure. In FIG. 5C, the left and right clamps 164a, 164b are in the closed, clamped position and the left and right clamps 164a, 164b define an opening narrower than the opening of the shoe base 162 or the diameter of the bone screw. In FIG. 5D, the locking rod has been rotated counter-clockwise and the external locking rod 168 has been removed above apertures 172a, 172b, allowing the center of the apertures 172a, 172b to be offset from the locking rod (collectively 168, 170) and left and right clamps 164a, 164b to pivot towards an open position. In FIG. 5E, the left and right clamps 164a, 164b have fully pivoted outwardly to the open position, wherein the opening created by the left and right clamps 164a, 164b is the same diameter as the diameter of opening of the shoe base 162, thereby allowing the bone screw 180 to be received within the superior/inferior blade 106. In FIG. 5F, the bone screw 180 has been fully received within the superior/inferior blade 106 and the locking rod has been rotated clockwise, driving the external locking rod 168 back into and self-centering the apertures 172a, 172b of the left and right clamps 164a, 164b. In FIG. 5F, the left and the right clamps 164a, 164b have fully pivoted back to the closed position and the diameter of the opening created by the left and right clamps 164a, 164b is less than the diameter of the bone screw shaft, thereby preventing the bone screw 180 from being able to be removed from the blade 106. In the closed position, the bone screw 180 is still operable to pivot and rotate relative to the blade 106, allowing the bone screw 180 to be driven into a pedicle while locked into the blade 106.

By allowing the bone screw 180 to pivot and rotate within the blade 106, the bone screw 180 may be loosely driven into the pedicle without the blade 106 being in position and then the blade 106 may be locked around the bone head screw for final tightening/driving of the bone screw 180. The degrees of rotational freedom and translation created by the ball joint mechanisms (not shown), allow one or more blades 106 to be clamped around one or bone screws that may be set in the pedicle in a large range of orientations independent of each other.

Figure 6A:
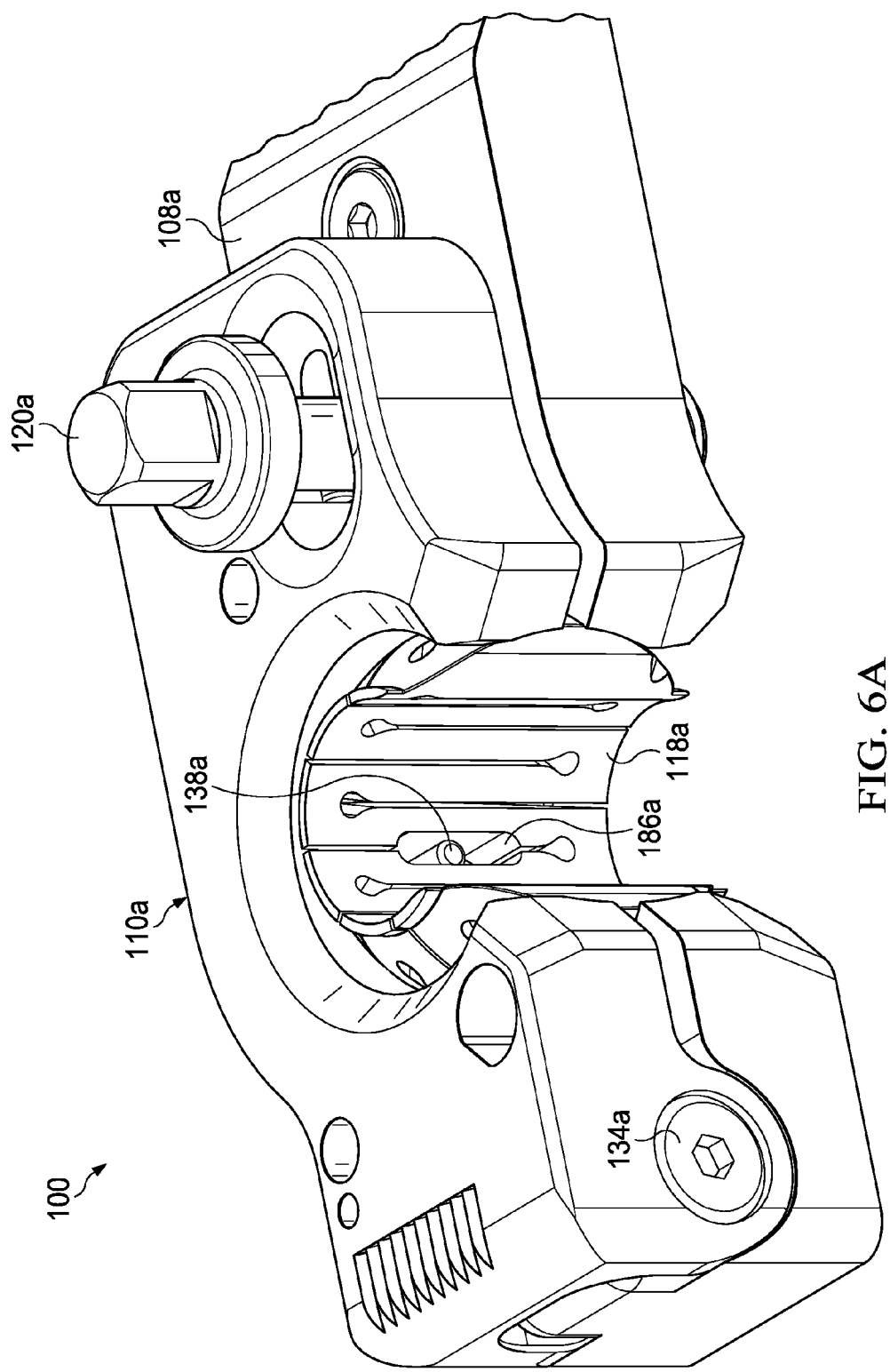
FIG. 6A depicts a perspective view of a superior/inferior clamp arm of the frame of the integrated retractor-distractor system of FIG. 1, in accordance with one embodiment of the present disclosure.

FIG. 6A depicts a perspective view of the superior clamp arm 110a of the frame 102 of the integrated retractor-distractor system 100 of FIG. 1, in accordance with one embodiment of the present disclosure. FIG. 6A depicts the superior sliding arm 108a although the inferior sliding arm (not shown) would comprise the same components.

As shown in FIG. 6A, the ball joint 118a comprises an elongated and widened slot 186a opposite the openings of the ball joint 118a, the sliding arm 108a, and the arm clamp 110a. Ball joint pin 138a extends from the sliding arm 108a into the ball joint 118a, allowing the ball joint 118a to rotate in three degrees of freedom while keeping the opening of the ball joint 118a aligned with the openings of the sliding arm 108a and the arm clamp 110a, thereby allowing the surgeon to easily "snap" the superior blade (not shown) into the sliding arm 108a. As previously discussed, when the ball joint lock 120a is rotated counter-clockwise, the lifting shoulder (not shown) of the ball joint lock 120a causes the arm clamp 110a to pivot upwardly about pivot pin 134a, allowing the ball joint 118a to pivot about the ball joint pin 138a.

Figure 6C:
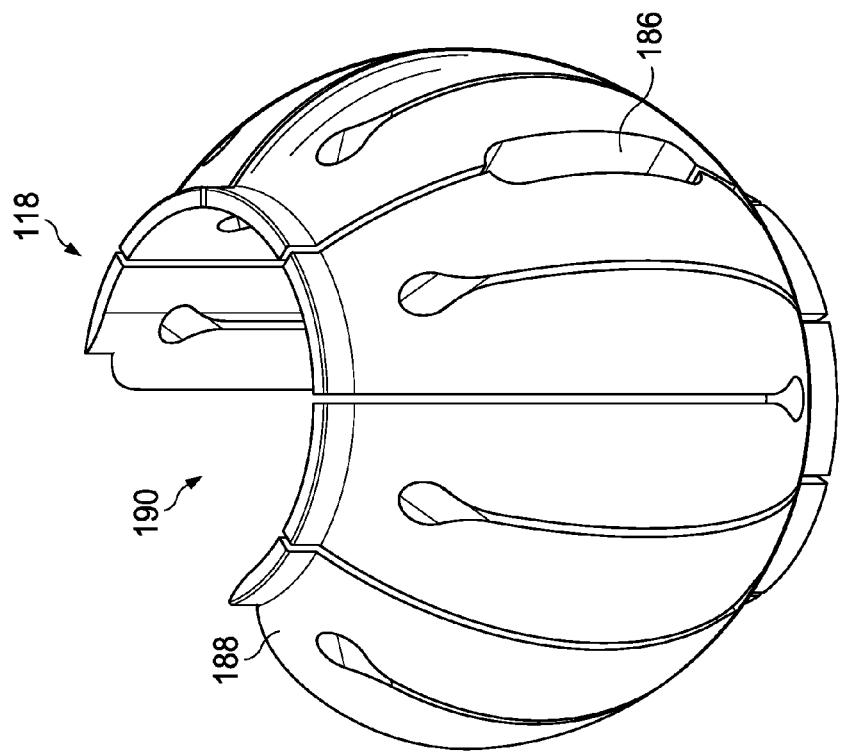
FIGS. 6B-6C depict perspective views of a ball joint of the superior clamp arm of FIG. 6A, in accordance with one embodiment of the present disclosure.
Figure 6B:
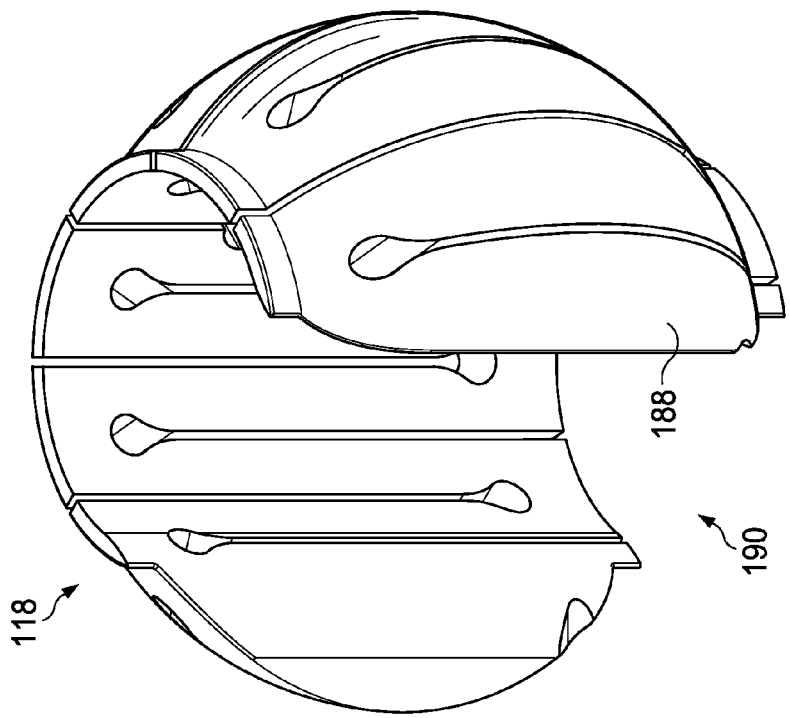

FIG. 6B and FIG. 6C depict perspective views of a ball joint 118 of the superior clamp arm 106a of FIG. 6A, in accordance with one embodiment of the present disclosure. The ball joint 118 may be any of the ball joints 118a, 118b, and 118c described earlier. As depicted in FIGS. 6B and 6C, the ball joint 118 may comprise an elongated and widened slot 186 opposite an opening 190 and a plurality of spring-loaded collets 188. When a superior/inferior blade or a medial blade (not shown) is received within the ball joint 118 at the opening 190 and clamped (tightened) to a locked position, spacing between the collets 188 disappear and an effective internal diameter of the ball joint 118 is reduced, thereby locking the ball joint 118 against the ball joint connection shaft (not shown) of the blade.

Figure 7A:
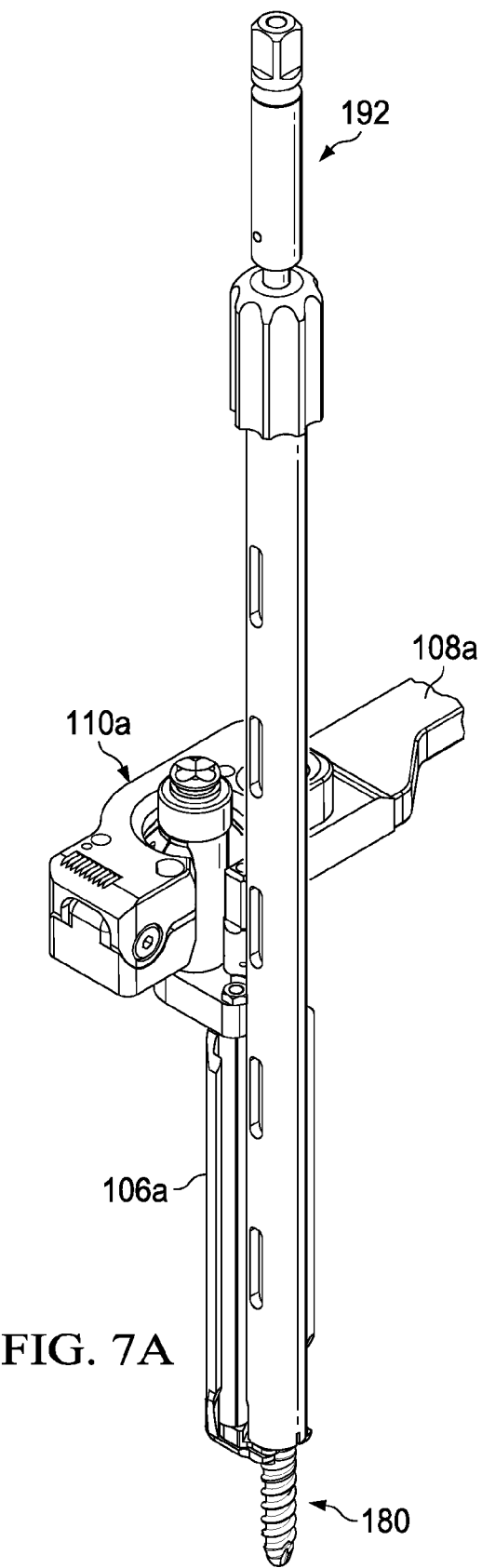
FIG. 7A depicts a partial perspective view of the inferior/superior clamp arm of FIG. 6A with a modular bone screw and a bone screw driver, in accordance with one embodiment of the present disclosure.

FIG. 7A depicts a partial perspective view of the superior blade 106a received within the superior sliding arm 108a and the superior clamp arm 110a of FIG. 6A with the modular bone screw 180 and a bone screw driver 192, in accordance with one embodiment of the present disclosure. In the context of the bone screw driver 192, "proximal" refers to closer to the user/surgeon, while "distal" refers to away from the user/surgeon.

After the superior blade 106a has been received within the superior sliding arm 108a and the superior clamp arm 110a and the bone screw 180 has been clamped within the superior blade 106a, the bone screw driver 192 may be removably attached to the head (not shown) of the bone screw 180 and the bone screw 180 may be driven/tightened to its final position in the pedicle.

Figure 7B:
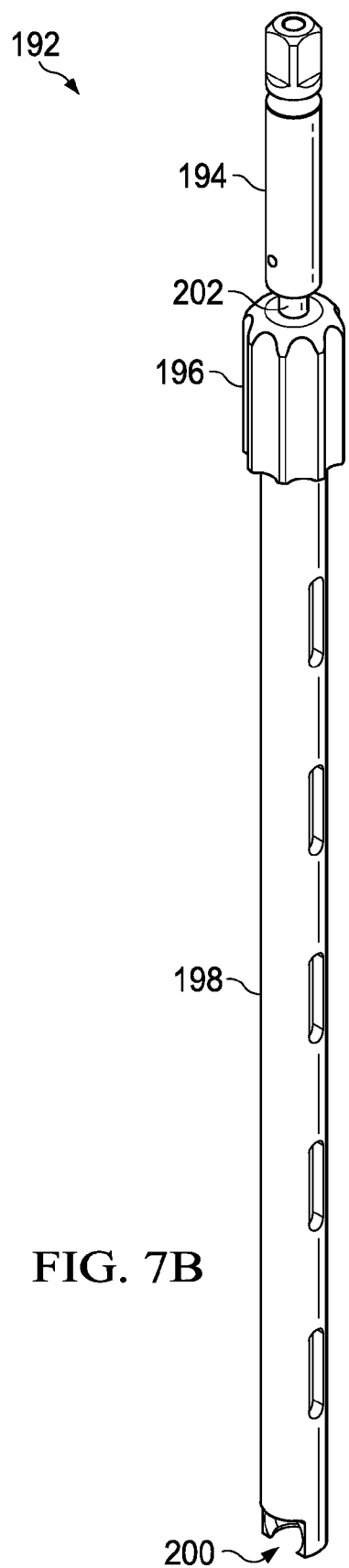
FIG. 7B depicts a perspective view of the bone screw driver of FIG. 7A, in accordance with one embodiment of the present disclosure.
Figure 7C:
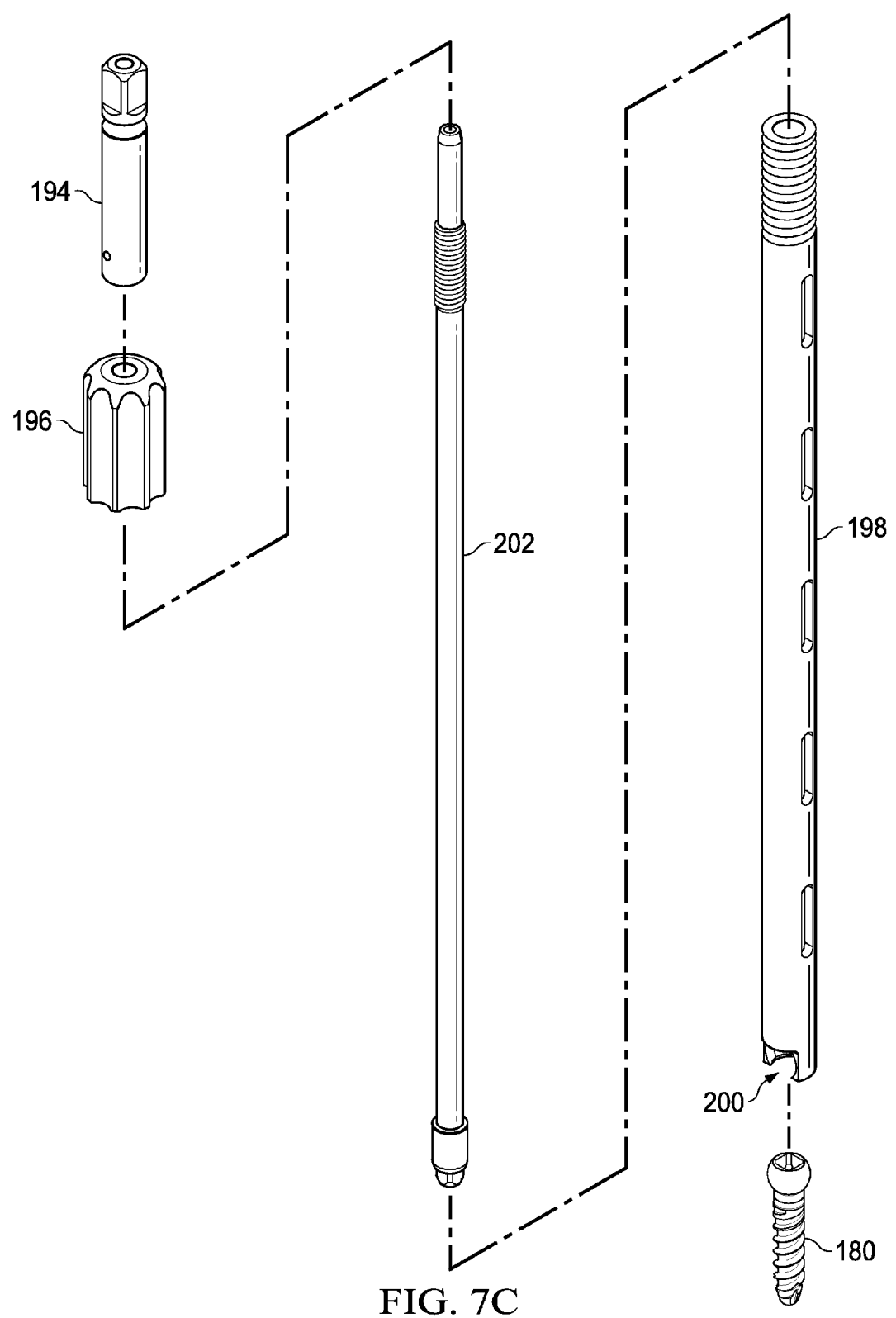
FIG. 7C depicts an exploded view of the bone screw driver of FIG. 7A, in accordance with one embodiment of the present disclosure.

FIG. 7B depicts a perspective view of the bone screw driver 192 of FIG. 7A, in accordance with one embodiment of the present disclosure. FIG. 7C depicts an exploded view of the bone screw driver 192 of FIG. 7A, in accordance with one embodiment of the present disclosure. The bone screw driver 192 may comprise a head 194 at a proximal end, an internal driver 202, a collar 196, and an external body 198 comprising an opening 200 defined within a sidewall of the external body 198 and located at a distal end. The internal driver 202 may be received within the external body 198 and is operable to rotate and translate within the external body 198. A proximal end of the internal driver 202 may be received within the head 194 and the collar 196 may be received over a threaded proximal end of the external body 198 and the internal driver 202.

The radius of the external body 198 may be sized to be approximately the same as the radius of the clamping mechanism encasement 166 depicted in FIG. 5A. The opening 200 may be approximately half the size of the circumference of the proximal end of the external body 198 and is sized to receive the head of the bone screw 180. This allows the bone screw driver 192 to be readily attached to and detached from the bone screw 180 that has already been surgically implanted into a patient. The external body 198 may comprise slots along its body to allow the internal driver 202 to be cleaned during surgery. The external body 198 may further comprise markings opposite the opening 200 so that the surgeon can easily determine where the opening 200 is located for receiving and removing the bone screw driver 192 over the bone screw 180, particularly during surgery.

In operation, when the collar 196 is rotated counter-clockwise, the internal driver 202 is translated proximally, thus removing the distal end of the internal driver 202 from within the opening 200. The bone screw driver 192 may then be received over the head of the bone screw 180 at the opening 200. After being received over the head of the bone screw 180, the bone screw driver 192 may be used to drive the bone screw 180 into appropriate tissue, such as the pedicle region of a vertebrae.

To drive the bone screw 180, the collar 196 may be rotated clockwise, thus translating the internal driver 202 distally until it mates with the head of the bone screw 180. The collar 196 may then be tightened further relative to the external body 198. After the collar 196 has been tightened, a removable driver (not shown) can be attached to the head 194 of the bone screw driver 192, rotating the internal driver 202 and the bone screw 180 clockwise and driving the bone screw 180 further into the pedicle.

After the bone screw 180 has been fully driven into the pedicle, the collar 196 may be rotated counter-clockwise, allowing the internal driver 202 to be translated proximally. When the internal driver 202 is translated proximally, the distal end of the internal driver 202 is withdrawn from the head of the bone screw 180 and the bone screw driver 192 may be removed from the bone screw 180 through the opening 200 in the sidewall of the external body 198. The configuration of the bone screw driver 192 advantageously allows the bone screw driver 192 to be affixed to the bone screw 180 in situ, drive the bone screw 180 into place, and then removed in situ without the risk of loosening the bone screw 180. Since the radius of the external body 198 is approximately the same as the radium of the clamping mechanism encasement 166 (as shown in FIG. 5A), the bone screw driver 192, the blade 106, and the bone screw 180 act as a unitary piece, thus allowing the surgeon to manipulate, retract, distract, and surgically install pedicle screws with a single assembly.

Figure 8:
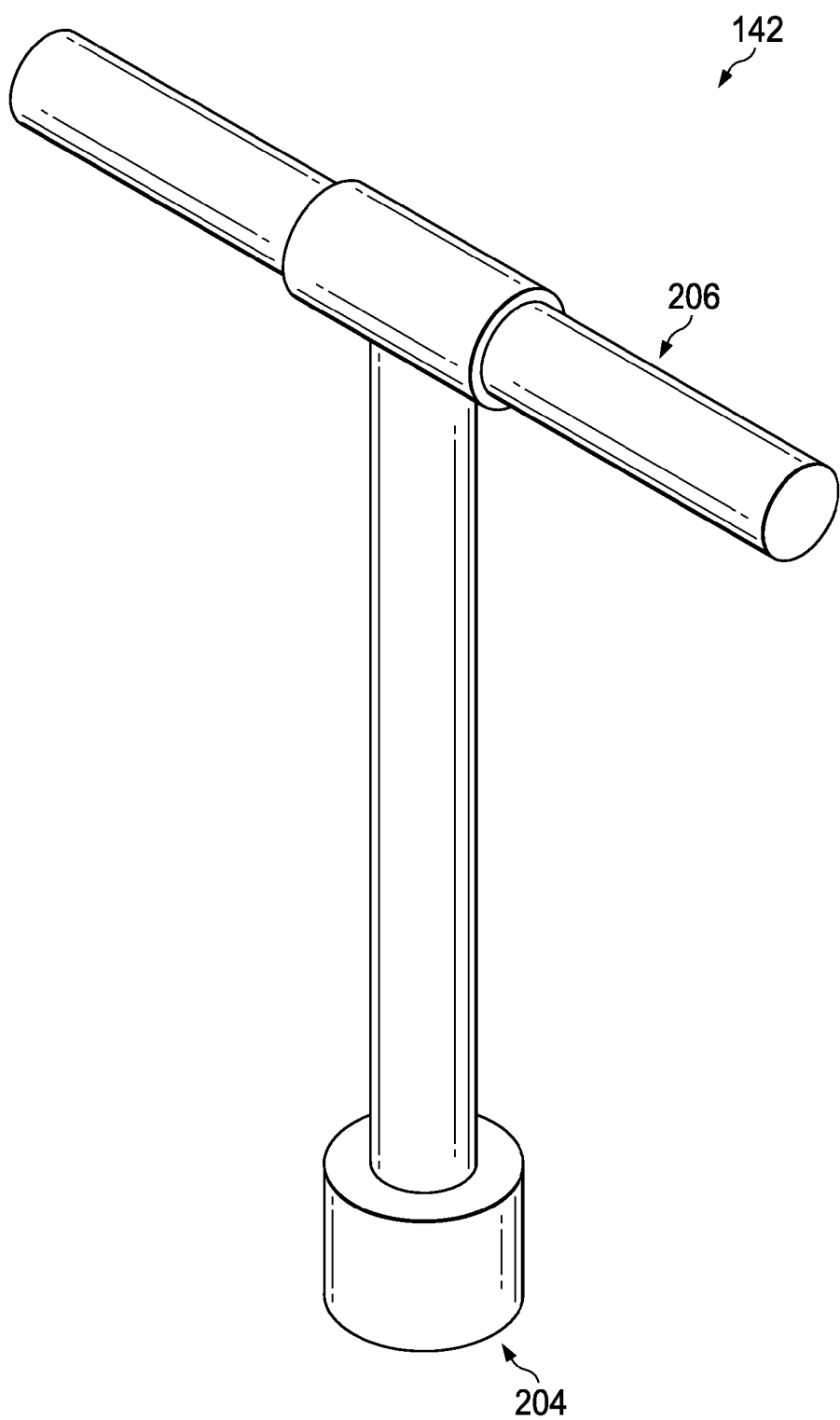
FIG. 8 depicts a perspective view of a driver, in accordance with one embodiment of the present disclosure.

FIG. 8 depicts a perspective view of the removable driver 142, in accordance with one embodiment of the present disclosure. In the context of the removable driver 142, "proximal" refers to closer to the user/surgeon, while "distal" refers to away from the user/surgeon. The driver 142 may comprise a recess 204 at a distal end and a handle 206 at a proximal end. The recess 204 may be a square recess, a hex recess, or any other shape operable to mate with a component to be driven.

In an embodiment, the driver 142 is a T-handle driver and the recess 204 may be sized and shaped to mate with and drive superior/inferior gearing drive 130 (FIG. 3A), the lateral/medial gearing drive 132 (FIG. 3A), the superior/inferior ball joint locks 120a, 120b (FIG. 2), and the pivot locking screw 128 (FIG. 2). The driver 142 may also be sized to drive the head 194 of the bone screw driver 192, although in some embodiments, a larger driver may be needed to drive the head 194 of the bone screw driver 192 in order to have sufficient torque to drive the bone screw into the pedicle.

Advantageously, the retractor-distractor system 100 allows a surgeon to make a small incision in the skin, insert the superior and proximal blades 106a, 106b through the incision, and then using the sliding arms 108a, 108b and the ball joints 118a, 118b, "toe-out" the proximal ends of the blades 106a, 106b so that the tissue under the skin is moved in order to expose a larger surgical area in the spine while still maintaining a small incision.

In addition, the retractor-distractor system 100 may be able to be disengaged from the implanted bone screws 180 in situ while maintaining the tissue retraction after a spinal implant cage is inserted. Then, the retractor-distractor system 100 allows extra retraction so that the proximal ends of the blades 106a, 106b may be moved away from the bone screws 180 so that a tulip head can be installed onto the heads of the bone screws 180 without losing the skin retraction. The medial blade 104 can be used to allow retraction on the medial/lateral side of the vertebral bodies.

The opening 200 of the bone screw driver 192 also allows the bone screw driver 192 to securely capture and detach from a bone screw 180 in situ, while providing multiple degrees of freedom in both rotation and translation through the ball joints 118a, 118b, and 118c. The superior/inferior blades 106a, 106b are easy to connect to the frame 102 at the ball joints 118a, 118b, and 118c and may be locked in place by compressing the ball joints.

Further, the retractor-distraction system 100 is re-usable and there are no components that are removed from the system 200 during surgery, preventing the possibility of losing any components or segments in the surgical wound.

One or more components of the retractor-distractor system 100 disclosed herein may be made from any of the following materials: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, TI-6Al-4V, stainless steel); (f) a radiolucent material (e.g., carbon fiber, PEEK or aluminum); or (g) any combination thereof.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A retractor-distractor system comprising:
    a frame comprising:
        a superior arm slidably coupled to and extending from the frame, the superior arm further comprising:
            a superior clamp arm pivotally coupled to a lateral end of the superior arm;
            a superior ball joint received between the superior clamp arm and the superior arm; and
            a superior ball joint lock operable to pivot the superior clamp arm proximate to the superior arm, thereby locking the orientation of the superior ball joint;
            wherein the superior arm, the superior clamp arm, and the superior ball joint each comprise an opening within their respective inferior sides, the openings operable to receive a modular blade operable to retract and distract tissue;
        an inferior arm slidably coupled to and extending from the frame, the inferior arm further comprising:
            an inferior clamp arm pivotally coupled to a lateral end of the inferior arm;
            an inferior ball joint received between the inferior clamp arm and the inferior arm;
            an inferior ball joint lock operable to pivot the inferior clamp arm proximate to the inferior arm, thereby locking the orientation of the inferior ball joint;
            wherein the inferior arm, the inferior clamp arm, and the inferior ball joint each comprise an opening within their respective superior sides, the openings operable to receive a modular blade operable to retract and distract tissue;
        wherein the frame is operable to slide the superior arm and the inferior arm in both superior and inferior directions relative to the frame.

2. The retractor-distractor system of claim 1, wherein the superior ball joint and the inferior ball joint each comprise a plurality of spring-loaded collets, wherein when the orientations of the superior ball joint and the inferior ball joint are locked, spacing between the plurality of spring-loaded collets disappears, reducing an effective internal diameter of the superior ball joint and the inferior ball joint.

3. The retractor-distractor system of claim 1 further comprising a first modular blade comprising:
    a distal end and a proximal end;
    a ball joint connecting shaft proximate to the proximal end;
    a retractor skin extending from the proximal end to the distal end; and
    wherein the first modular blade is operable to be removably coupled with the frame when the ball joint connecting shaft is received within the openings in the inferior sides of the superior arm, the superior clamp arm, and the superior ball joint.

4. The retractor-distractor system of claim 3, wherein the first modular blade further comprises a clamping mechanism proximate to the distal end and operable to releasably attach to a modular bone screw.

5. The retractor-distractor system of claim 3 further comprising a second modular blade comprising:
    a distal end and a proximal end;
    a ball joint connecting shaft proximate to the proximal end;
    a retractor skin extending from the proximal end to the distal end; and
    wherein the second modular blade is operable to be removably attached with the frame when the ball joint connecting shaft is received within the openings in the superior sides of the inferior arm, the inferior clamp arm, and the inferior ball joint.

6. The retractor-distractor system of claim 5, wherein the second modular blade further comprises a clamping mechanism proximate to the distal end and operable to releasably attach to a modular bone screw.

7. The retractor-distractor system of claim 1, wherein the frame further comprises a pivot arm slidably coupled to and extending from the frame, the pivot arm comprising:
    an upper pivot arm pivotally coupled to a lower pivot arm;
    a medial ball joint received between the upper pivot arm and the lower pivot arm;
    a pivot locking screw operable to pivot a lateral end of the upper pivot arm proximate to a lateral end of the lower pivot arm, thereby locking the orientation of the medial ball joint;
    wherein the upper pivot arm, the lower pivot arm, and the medial ball joint each comprise an opening about their respective lateral sides operable to receive a modular blade.

8. The retractor-distractor system of claim 7 further comprising a modular blade comprising:
    a distal end and a proximal end;
    a ball joint connecting shaft proximate to the proximal end; and
    a retractor skin extending from the proximal end to the distal end;
    wherein the modular blade is operable to be removably attached with the frame when the ball joint connecting shaft is received within the openings in the lateral sides of the upper pivot arm, the lower pivot arm, and the medial ball joint.

9. The retractor-distractor system of claim 7, wherein the frame further comprises an internal gearing system, wherein the internal gearing mechanism is operable to slide the pivot arm in medial and lateral directions.

10. The retractor-distractor system of claim 1, wherein the superior arm comprises a superior ball joint locking pin extending from the inferior side and into the opening of the superior arm, wherein the superior ball joint comprises an elongated slot opposite the opening of the superior ball joint, and wherein the ball joint locking pin extending from the superior arm is operable to be received within the elongated slot of the superior ball joint, thereby allowing the superior ball joint to rotate in three degrees of freedom while keeping the opening of the superior ball joint aligned with the openings of the superior arm and the superior arm clamp.

11. The retractor-distractor system of claim 10, wherein the elongated slot is a widened portion of the collet.

12. The retractor-distractor system of claim 1, wherein the inferior arm comprises an inferior ball joint locking pin extending from the superior side and into the opening of the inferior arm, wherein the inferior ball joint comprises an elongated slot opposite the opening of the inferior ball joint, and wherein the ball joint locking pin extending from the inferior arm is operable to be received within the elongated slot of the inferior ball joint, thereby allowing the inferior ball joint to rotate in three degrees of freedom while keeping the opening of the inferior ball joint aligned with the openings of the inferior arm and the inferior arm clamp.

13. The retractor-distractor system of claim 12, wherein the elongated slot is a widened portion of the collet.

14. The retractor-distractor system of claim 1, wherein the superior ball joint lock and the inferior ball joint lock each comprise a head at a proximal end and a shaft at a distal end and a lifting shoulder positioned approximately halfway about the shaft, wherein the lifting shoulder of the superior ball joint lock is positioned between the superior arm and the superior arm clamp and is operable to pivot the superior arm clamp away from the superior arm, thereby releasing the orientation of the superior ball joint, and wherein the lifting shoulder of the inferior ball joint lock is positioned between the inferior arm and the inferior arm clamp and is operable to pivot the inferior arm clamp away from the inferior arm, thereby releasing the orientation of the inferior ball joint.

15. The retractor-distractor system of claim 1, wherein the frame further comprises an internal gearing system, wherein the internal gearing mechanism is operable to slide the inferior arm and the superior arm in both superior and inferior directions.

\* \* \* \* \*